United States Patent [19]

Lähetkangas

[11] Patent Number: 5,240,857
[45] Date of Patent: Aug. 31, 1993

[54] TEMPERATURE-GRADIENT INCUBATOR FOR STUDYING TEMPERATURE-DEPENDENT PHENOMENA

[75] Inventor: Alpo Lähetkangas, Espoo, Finland

[73] Assignee: Biodata OY, Helsinki, Finland

[21] Appl. No.: 754,510

[22] Filed: Sep. 3, 1991

[30] Foreign Application Priority Data

Mar. 6, 1989 [FI] Finland ................................. 891050

[51] Int. Cl.$^5$ .......................... C12M 1/02; F28F 1/32
[52] U.S. Cl. .................................. 435/316; 435/809; 435/287; 165/146; 165/171; 165/185
[58] Field of Search ............... 435/284, 285, 287, 316, 435/809; 165/146, 171, 185

[56] References Cited

U.S. PATENT DOCUMENTS

| | | | |
|---|---|---|---|
| 3,770,591 | 11/1973 | Boirat et al. | 435/809 |
| 3,801,467 | 4/1974 | Nobe et al. | 165/30 |
| 4,679,615 | 7/1987 | Livne | 165/146 |
| 4,865,987 | 9/1989 | Seppo | 435/290 |

Primary Examiner—Robert J. Warden
Assistant Examiner—T. A. Trembley
Attorney, Agent, or Firm—Christensen, O'Connor Johnson & Kindness

[57] ABSTRACT

The invention relates to a temperature-gradient incubator for studying temperature dependent phenomena, such as temperature ranges for the growth of microbes, comprising a temperature-gradient plate (10) serving as a reaction substrate and heat transfer elements (17 and 18) extending along the opposite edges of the temperature-gradient plate (10) for the heating and cooling of the edges of the temperature-gradient plate (10). Each heat transfer element (17 or 18) is provided with two passages for the circulation of a heating and/or cooling medium. Gable elements (9, 16) connect the passages to each other. The gable elements (9, 16) and pipe joint elements (6, 13) are separated from the ends of heat transfer elements (17, 18) by rubber sheets (1) which serve to provide heat insulation and sealing and are provided with holes (2, 3) for the circulation of a medium.

7 Claims, 2 Drawing Sheets ced direct# TEMPERATURE-GRADIENT INCUBATOR FOR STUDYING TEMPERATURE-DEPENDENT PHENOMENA

TECHNICAL FIELD

The present invention relates to a temperature-gradient incubator used for studying temperature-dependent phenomena, comprising a temperature-gradient plate serving as a reaction substrate and heat transfer elements extending along the opposite edges of the temperature-gradient plate for heating or cooling the edges of the temperature-gradient plate, at least one of said heat transfer elements being provided with two passages for the circulation of a heating and/or cooling medium.

BACKGROUND ART

When studying the dependence of biological activities on temperature, temperature-gradient incubators are useful devices in a variety of ways. In nearly all solutions described in literature, a temperature gradient is produced by heating one end of an elongated metal body to a constant temperature. The other end is either subjected to free cooling or cooled to a constant temperature. By virtue of heat conduction, the metal body generates a more or less linear temperature gradient which can be utilized for studying the growth and activity of microbes at continuously varying temperatures. It is essential to produce a uniform temperature gradient and a complete temperature-gradient linearity over the entire area of a temperature-gradient plate as non-linearity results in visible curving of isotherms parallel to the longer side of a gradient plate and causes errors in the determination of temperature ranges for microbe cultures.

The temperature-gradient incubators described in literature and intended for microbiological application include primarily two types of devices. One type of devices are intended for growing microbes in fluid cultures, the other for growing in agar jelly or some other "solid" culture medium. In the latter type, it is possible to produce a stepless or continuous temperature gradient. A typical characteristic in commercially available equipment is that temperature varies along the greatest dimension of a metal body whereby temperature distribution will be sufficiently stabilized. If the culture capacity should be increased in lateral direction, either temperature distribution will be difficult to control or the equipment will large and bulky provided that the longitudinal direction will still be maintained as gradient direction. In general, the capacity of prior known temperature-gradient incubators ranges from a single culture to a few cultures per run.

The publication Can. J. Microbiol., vol. 19, No. 9, 1973 pp. 1161-1165 discloses a temperature-gradient incubator wherein the ends of circulation passages are connected by means of flow channels, built inside the corners of one end of a massive temperature-gradient plate, said channels being covered with plates. Between the cover plates and the end of gradient plate is a thin rubber seal. A result of this construction is that the transfer of heat within the corner regions of a gradient plate between the medium and the gradient plate and also between the gradient plate and the environment is different from the transfer of heat within the central region of a gradient plate. The same is true also within those corner regions of a gradient plate in which a medium is introduced into the gradient plate passages since the supply tubes are connected directly to the ends of the passages. In order to achieve an improved linearity for temperature gradient isotherms, this prior known gradient plate has a substantial thickness and the heat transfer elements are mounted along the short sides of a gradient plate. Thus, the linearity of isotherms is accomplished at the cost of high energy consumption and limited testing capacity.

An object of the invention is to provide an improved temperature-gradient incubator with a construction as simple as possible, which is capable of achieving an improved linearity for isotherms without resorting to great plate thickness and having to have a low testing capacity.

DISCLOSURE OF THE INVENTION

According to the invention, this object is achieved by providing a plate with heat transfer elements running the length of two opposite edges of the plate. The elements can either heat or cool either edge of the plate. That is, one edge of the plate can be cooled and the other edge heated, or both edges may be heated or cooled, thereby inducing a desired temperature gradient in the plate.

At least one of the heat transfer elements contains two circulation passages that are in fluid communication. The fluid communication is achieved by means of a gable element that directs the flow of fluid from the end of the first circulation passage into the end of the second circulation passage. The gable element is separated from the circulation passages by a sealing element that prevents the leakage of fluid, as the fluid is directed from the first passage into the second circulation passage, and the sealing element also serves to insulate the fluid from the gain or loss of heat, as the fluid is directed from the first circulation passage into the second circulation passage.

Fluid is introduced into the first circulation passage by a first pipe joint element, and is drained away from the second circulation passage by a second pipe joint element. A sealing element, as previously described, between the pipe joint elements and circulation passages serves to prevent the leakage of fluid, and to prevent the gain or loss of heat by the fluid. In the preferred embodiment, the sealing element is composed of rubber. To induce the proper temperature gradient in the plate, the fluid is maintained at a predefined, substantially steady temperature as it is circulated through the circulation passages.

BRIEF DESCRIPTION OF THE DRAWINGS

One embodiment of the invention will now be described in more detail with reference made to the accompanying drawings, in which.

DETAILED DESCRIPTION OF THE PREFERRED EMBODIMENT

Figure 2:
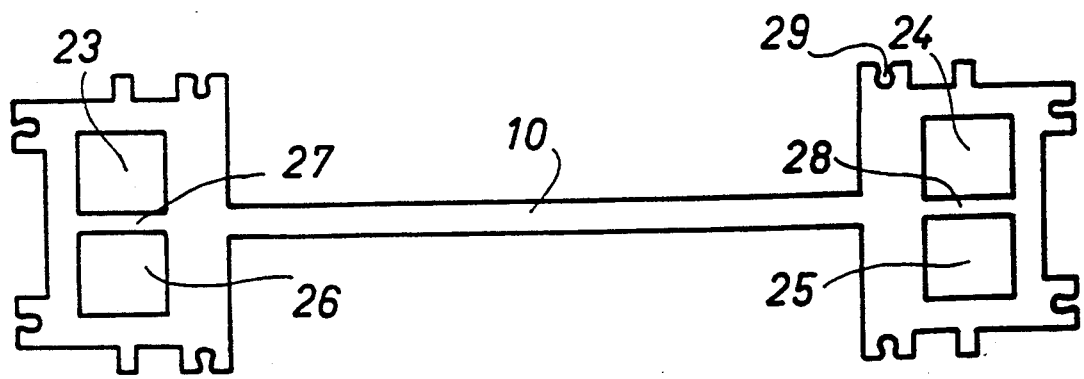
FIG. 2 shows an incubator core according to a preferred embodiment of the invention in an end view.

In the present case, the incubator core comprises a single metal profile having a cross-sectional configuration as shown in FIG. 2. It is obvious that the incubator core can also be made of several components. Particularly, a plate 10 can be a separate component, the passage sections being pressed against the opposite edge regions thereof. The reaction analysis base comprises a rectangular temperature-gradient plate 10, provided with heat transfer elements 17 and 18 along its longer edges. Each heat transfer element is provided with two passages 24, 25 and 23, 26, respectively. The passages are separated from each other by means of a partition 28, respectively 27. The first ends of the circulation passages are connected in mutual flow communication by means of a gable element 16, respectively 9. The second ends of the circulation passages are fitted with a pipe joint element 13, respectively 6. The pipe joint elements 6 and 13 are provided with connectors 4, 11 for inlet flow and connectors 5, 12 for outlet flow.

Figure 1:
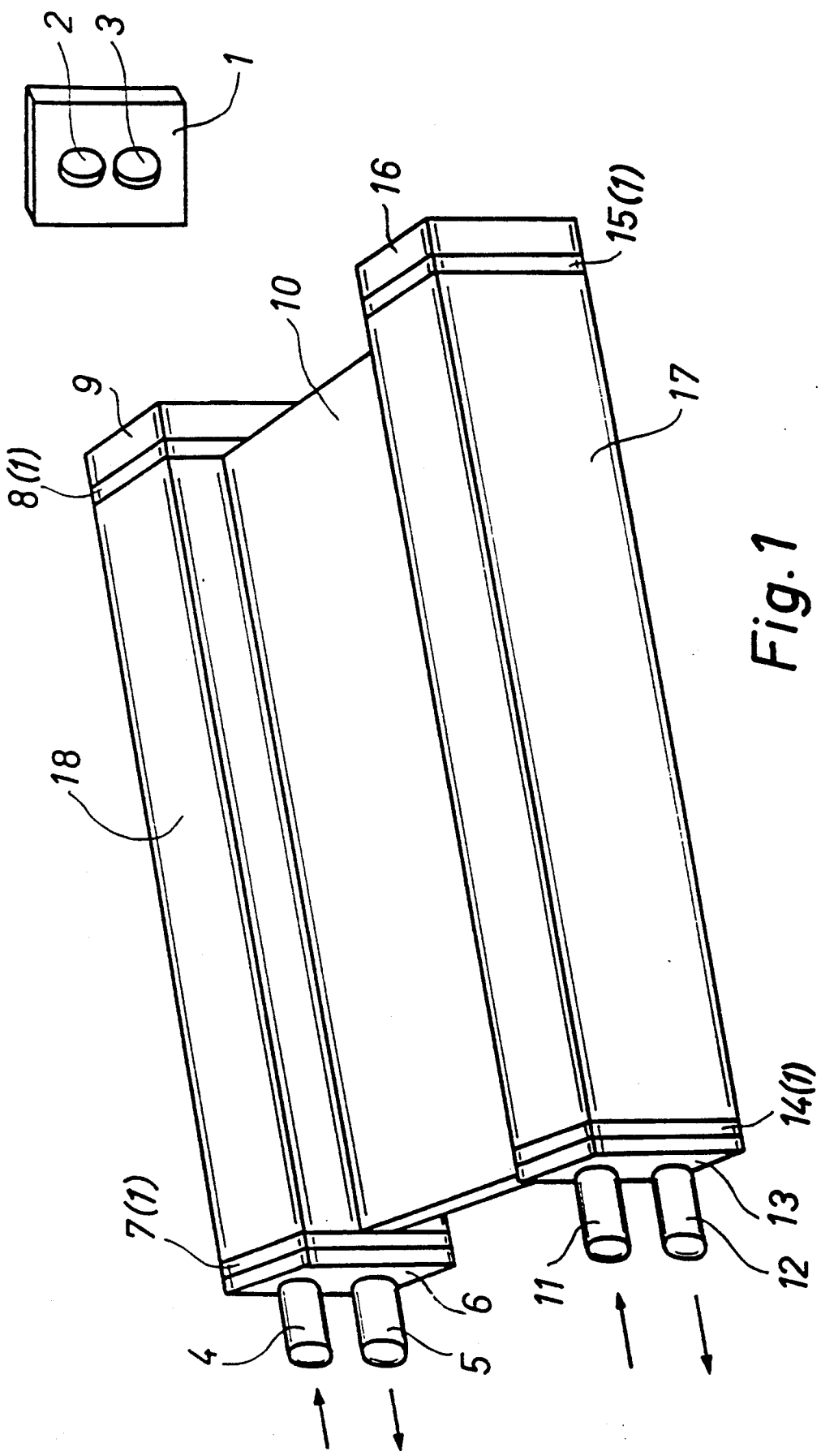
FIG. 1 shows an incubator of the invention in prespective view.

Between pipe joint element 6 and the end of heat transfer element 18 is fitted a rubber sheet 7. Likewise, between pipe joint element 13 and the end of heat transfer element 17 is fitted with a rubber sheet 14. Between the other end of heat transfer element 18 and gable element 9 is fitted a rubber sheet 8. Between the other end of heat transfer element 17 and gable element 16 is fitted a rubber sheet 15. In FIG. 1, reference numeral 1 indicates a separate rubber sheet, provided with holes at the ends of circulation passages 23, 26 and respectively 24, 25. The rubber sheets serve both as heat insulation and as a seal. By selecting a proper thickness for rubber sheets 1 it is possible to create a desired heat insulation effect at the corners of gradient plate 10 for thus controlling and linearizing the isotherms produced in gradient plate 10. The thickness of rubber sheets 1 is e.g. 5 mm.

Figure 3:
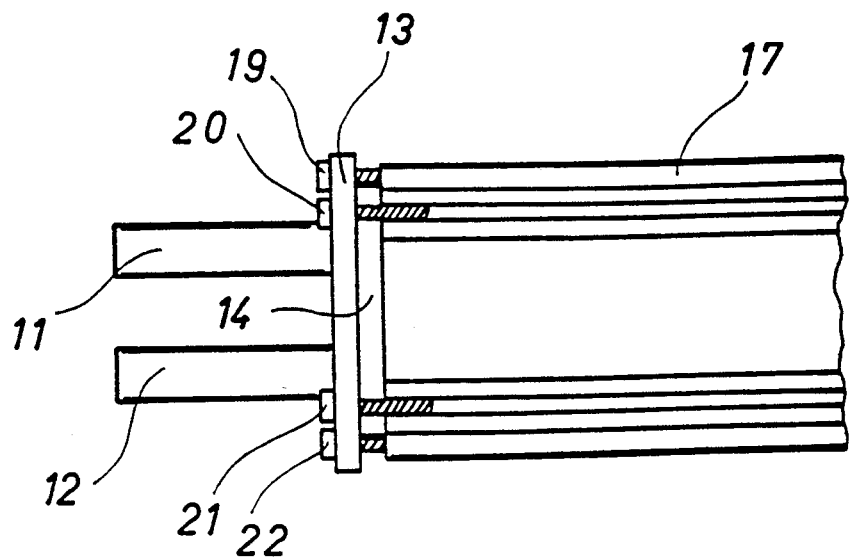
FIG. 3 is a closer view of one detail of an incubator at the lower left-hand side or the incubator shown in FIG. 1.

As shown in FIGS. 2 and 3, the surface of heat transfer elements 17, 18 is provided with grooves 29 to be engaged by the threaded portions of fastening screws 19-22. Thus, pipe joint elements 6, 13 and gable elements 9, 16 can each be fastened with four screws 19-22.

The circulation of a heating or cooling medium in the passages of heat transfer elements 17 and 18 maintains a uniform temperature over the entire length of heat transfer elements 17 and 18. In addition to sealing effect, a particular function of rubber sheets 1 is to prevent the conductive transfer of heat between the corners of gradient plate 10 and the environment.

Temperature gradient is produced in plate 10 by introducing fluids of different temperatures into the passages of heat transfer elements 17 and 18. Fluid is supplied by means of a pump (not shown) e.g. into a tube 11 for passing the fluid through aperture 2 in rubber sheet 14 (1) into a passage 24 (FIG. 2). Gable element 16 deflects the fluid from passage 24 to passage 25 for discharging the fluid through outlet tube 12 into a fluid bath, wherein the fluid temperature is maintained precisely at a desired value. A thin metal partition 28 between passages 24 and 25 serves to equalize a temperature difference between inlet and outlet fluid, thus giving its small contribution to improved linearity of the device.

The invention provides an arrangement for mounting heat transfer elements 17 and 18 along the long edges of gradient plate 10 without the loss of linearity. At the same time, all connecting tubes 4, 5 and 11, 12 can be positioned side by side along one of the short sides of the device which naturally facilitates disposition and handling of the device while providing a construction which is simple to obtain.

The invention also provides an arrangement, wherein the temperature of just one edge of gradient plate 10 is standardized by means of fluid circulation, the other edge having its temperature standardized e.g. by means of electric heating elements.

The temperature-gradient incubator core is positioned in a conventionally heat-insulated housing (not shown).

I claim:

1. A temperature-gradient incubator for studying temperature-dependent phenomena, such as temperature ranges for the growth of microbes, comprising a temperature-gradient plate (10) serving as a reaction substrate and heat transfer elements (17 and 18) extending along opposite sides of the temperature-gradient plate for heating or cooling edges of the temperature-gradient plate, at least one of said heat transfer elements being provided with two circulation passages (23, 26 or 24, 25) for the circulation of a heating and/or a cooling medium, wherein the two circulation passages each have two ends, wherein the first ends of the two circulation passages are connected in mutual flow communication by means of a flow channel running through a running through a separate gable element (9 or 16), wherein said separate gable element (9 or 16) is separated from the end of heat transfer element (18 or 17) by means of elements (1, 8 or 15) serving to provide heat insulation and to prevent leakage of said heating or cooling medium, and the second ends of the two circulation passages are provided with a pipe joint element (4, 5, 6 or 11, 12, 13) separated from the end of heat transfer element (18 or 17) by means of a different element (1; 7 or 14) serving to provide heat insulation and to prevent leakage of said heating and/or cooling medium, wherein said different element (1, 7 or 14) comprises a rubber sheet (1), provided with holes (2, 3) at the ends of the two circulation passages (24, 25 or 23, 26).

2. An incubator as set forth in claim 1, wherein said pipe joint elements (6; 13) are provided with connectors 4, 5; 11, 12) for inlet and outlet flow.

3. An incubator as set forth in claim 2, wherein said temperature-gradient plate (10) is rectangular shaped and said heat transfer elements (17, 18) are mounted along the longer edges of said temperature-gradient plate (10).

4. An incubator as set forth in claim 2, wherein the surface of said at least one heat transfer element (17, 18) is provided with grooves (29) to be engaged by the threaded portion of fastening screws (19-22) for the separate gable element (9, 16) and pipe joint element (6, 13).

5. An incubator as set forth in claim 1, wherein said temperature-gradient plate (10) is rectangular shaped and said heat transfer elements (17, 18) are mounted along the longer edges of said temperature-gradient plate (10).

6. An incubator as set forth in claim 5, wherein the surface of said at least one heat transfer element (17, 18) is provided with grooves (29) to be engaged by the threaded portion of fastening screws (19-22) for the separate gable element (9, 16); and pipe joint element (6; 13).

7. An incubator as set forth in claim 1 wherein the surface of said at least one heat transfer element (17, 18) is provided with grooves (29) to be engaged by the threaded portion of fastening screws (19-22) for the separate gable element (9; 16) and pipe joint element (6; 13).

* * * * *

UNITED STATES PATENT AND TRADEMARK OFFICE
CERTIFICATE OF CORRECTION

PATENT NO. : 5,240,857      Page 1 of 2
DATED : August 31, 1993
INVENTOR(S) : A. Lähetkangas It is certified that error appears in the above-identified patent and that said Letters Patent is hereby corrected as shown below:

COLUMN    LINE

On the title page, item
[56]           Ref. 5           Please add --3,535,208  10/1970  Yuji Sasaki et al.--

[56]           Ref. 6           Please add --4,195,131  3/1980  Gary R. Papas--

[56]           Ref. 1           Please add --A2 0290722  11/1988  European--

[56]           1st Publn.       Please add --*J. Appl. Bact.* Vol. 36, 1973, G.J.K. Packer et al.:
"Other"        Publications"    "Design of a Temperature Gradient Incubator" pp. 173-177.--

[56]           2nd Publn.       Please add --*Can. J. Microbiol.* Vo. 19, 1973, J.R. Matches et
"Other"        Publications"    al: "Temperature-gradient Incubator for the Growth of
                                Clostridia" pp. 1161-1165.--

4              23               delete "running through a"
(Claim 1       Line 15)

UNITED STATES PATENT AND TRADEMARK OFFICE
CERTIFICATE OF CORRECTION

PATENT NO. : 5,240,857
DATED : August 31, 1993
INVENTOR(S) : A. Lähetkangas It is certified that error appears in the above-identified patent and that said Letters Patent is hereby corrected as shown below:

| COLUMN | LINE | |
|---|---|---|
| 4 (Claim 1 | 27 Line 19) | "or" should read --and/or-- |
| 4 (Claim 2 | 40 Line 3) | "4, 5; 11, 12)" should read --(4, 5; 11, 12)-- |
| 4 (Claim 7 | 62 Line 1) | "claim 1" should read --claim 1,-- |

Signed and Sealed this

Twenty-second Day of March, 1994

Attest:

BRUCE LEHMAN

Attesting Officer     Commissioner of Patents and Trademarks